United States Patent
Han et al.

(10) Patent No.: US 6,333,332 B1
(45) Date of Patent: Dec. 25, 2001

(54) STABILIZED PHARMACEUTICAL COMPOSITIONS CONTAINING BUPROPION HYDROCHLORIDE

(75) Inventors: Chien-Hsuan Han, Sunnyvale; Gary Liaw, Torrance, both of CA (US)

(73) Assignee: Impax Laboratories, Inc., Hayward, CA (US)

( * ) Notice: Subject to any disclaimer, the term of this patent is extended or adjusted under 35 U.S.C. 154(b) by 0 days.

(21) Appl. No.: 09/645,602

(22) Filed: Aug. 25, 2000

(51) Int. Cl.[7] .................................................. A61K 31/51
(52) U.S. Cl. .................... 514/276; 514/345; 514/565; 514/649; 424/451; 424/464; 424/465; 424/489
(58) Field of Search ....................... 424/489, 451, 424/464, 465; 514/345, 276, 649, 565

(56) References Cited

U.S. PATENT DOCUMENTS 4,743,450 * 5/1988 Harris et al. ..................... 424/440
5,731,000 * 3/1998 Ruff et al. ........................ 424/451
5,968,553 * 10/1999 Maiyta et al. .................... 424/474
6,153,223 * 11/2000 Apelian et al. ................... 424/489

* cited by examiner

Primary Examiner—James H. Reamer
(74) Attorney, Agent, or Firm—Arent Fox Kintner Plotkin Kahn

(57) ABSTRACT

This invention is directed to stabilized pharmaceutical preparations containing bupropion hydrochloride. The preferred stabilizers comprise salts of organic bases including those selected from the group consisting of creatinine hydrochloride, pyridoxine hydrochloride, and thiamine hydrochloride. Another stabilizer utilized includes a salt of an inorganic acid such as potassium phosphate monobasic. The compositions retain at least 80% of the initial potency of bupropion hydrochloride after one week at 60° and 75% relative humidity (RH), as well as four or twelve weeks at 40° C. and 75% RH.

55 Claims, No Drawings

STABILIZED PHARMACEUTICAL COMPOSITIONS CONTAINING BUPROPION HYDROCHLORIDE

FIELD OF THE INVENTION

This invention is directed to stabilized pharmaceutical preparations containing bupropion hydrochloride.

BACKGROUND OF THE INVENTION

Bupropion hydrochloride is a common chloropropiophenone antidepressant, most recently found useful for helping patients stop smoking. See PCT Application No. WO 99/38,499. Novel methods of making bupropion hydrochloride include those taught by Mehta. See U.S. Pat. Nos. 3,819,706 and 3,885,046. Relative to conventional antidepressants, bupropion hydrochloride has no significant sympathomimetic, sympatholytic, anticholinergic or cardiovascular effects. Bupropion hydrochloride is sold in immediate release, modified release and extended release tablet forms. Regardless of its form, stability of bupropion hydrochloride is affected by a number of factors including formulation microenvironments and storage conditions.

Various bupropion hydrochloride formulations have been proposed in the art, designed to increase its stability. For example, one group reports that degradation can be inhibited or prevented by including in the formulation stabilizers such as L-cysteine hydrochloride, glycine hydrochloride, malic acid, sodium metabisulfite, citric acid, tartaric acid and L-cystine dihydrochloride. See U.S. Pat. Nos. 5,358,970 and 5,763,493. The same group also reports that degradation of bupropion hydrochloride can be inhibited by use of stabilizers including ascorbic acid or isoascorbic acid. See U.S. Pat. Nos. 5,541,231 and 5,731,000. Another group has reported that the drug can be stabilized by formulating it with inorganic acids such as hydrochloric acid, phosphoric acid, nitric acid and sulfuric acid or combinations thereof. See U.S. Pat. No. 5,968,553 and PCT Application No. WO 99/33,456. Still others have reported that substances such as fumaric acid can inhibit degradation of bupropion hydrochloride. See PCT Application No. WO 99/33,457.

This invention is directed to pharmaceutical formulations of bupropion hydrochloride (as the drug or active ingredient), in which the stability of the bupropion hydrochloride is augmented by the addition of a pharmaceutically acceptable stabilizer in an amount effective to increase stability.

SUMMARY OF THE INVENTION

One of the objectives of the present invention is to provide a pharmaceutical composition comprising bupropion hydrochloride and a pharmaceutically acceptable stabilizer in an effective stabilizing amount, in which at least about 80% to about 98% of an initial potency of the bupropion hydrochloride in the composition is maintained after storage for one week at 60° C. and 75% relative humidity. The stabilizer is selected from the group consisting of a salt of an organic base, such as creatinine hydrochloride, pyridoxine hydrochloride and thiamine hydrochloride, and a salt of an inorganic acid, such as potassium phosphate monobasic.

The present invention also provides for a method of stabilizing bupropion hydrochloride in a pharmaceutical composition so that at least about 80% to about 98% of the potency of bupropion hydrochloride is maintained after storage for one week at 60° C. and 75% relative humidity. This method comprises the step of mixing bupropion hydrochloride with a pharmaceutically acceptable stabilizer in an effective stabilizing amount. The method utilizes a dry blend of bupropion hydrochloride, a pharmaceutically acceptable stabilizer, and other pharmaceutically acceptable excipients.

Another objective of the present invention includes providing a pharmaceutical composition comprising bupropion hydrochloride and a pharmaceutically acceptable stabilizer in an effective stabilizing amount, in which at least about 80% to about 98% of an initial potency of the bupropion hydrochloride in the composition is maintained after storage for 4 or 12 weeks at 40° C. and 75% relative humidity, wherein the stabilizer is selected from the group consisting of a salt of an organic base, such as creatinine hydrochloride, pyridoxine hydrochloride and thiamine hydrochloride, and a salt of an inorganic acid, such as potassium phosphate monobasic.

A further objective of the present invention includes a method of stabilizing bupropion hydrochloride in a pharmaceutical composition so that at least about 80% to about 98% of the potency of bupropion hydrochloride is maintained after storage for 4 or 12 weeks at 40° C. and 75% relative humidity. This method comprises the step of mixing a dry blend of bupropion hydrochloride with a pharmaceutically acceptable stabilizer in an effective stabilizing amount.

DETAILED DESCRIPTION OF THE INVENTION

Bupropion hydrochloride is disclosed in the Merck Index, 12$^{th}$ Edition, 1996, entry no. 1523. It is known chemically as β-2-(tert-butylamino)-3'-chloropropiophenone hydrochloride. See U.S. Pat. Nos. 3,819,706 and 3,885,046.

Stabilizer, as the term is used herein, means a compound that inhibits or prevents degradation of bupropion hydrochloride so that it can be used in a pharmaceutical preparation while retaining much of its potency. Stabilizers useful in accordance with the present invention retain at least 80% of the potency of bupropion hydrochloride and up to 98% percent potency after four to twelve weeks of storage at 40° C. and 75% RH, or after one week of storage at 60° C. and 75% RH.

Indeed, the stabilizers of the present invention are contemplated, within the context of the present invention, to be used with any appropriate pharmaceutical preparation and active ingredient, so that the active ingredient's stability in the pharmaceutical preparation is augmented. In a preferred embodiment, the active ingredient is bupropion hydrochloride; yet any active ingredient whose stability can be augmented, specifically in a pharmaceutical preparation, by the stabilizers of the present invention is contemplated.

The percentage of maximum stability product of bupropion hydrochloride is the amount of bupropion hydrochloride product remaining in the preparation relative to the amount of bupropion hydrochloride product in the formulation. Thus, for example, if a tablet initially contains 150 mg of bupropion hydrochloride (labeled amount) at the time of preparation, at least about 135 mg of bupropion hydrochloride (90%) remains in the tablet after one week's storage at 60° C. and about 75% RH.

The amount of active ingredient in the formulation after storage may be determined using standard procedures such as high performance liquid chromatography (HPLC) or other validated methods.

Maximum impurity of the product is defined as the maximum degradation product among all other relatively smaller degradation products. The total impurity is defined as the sum of all degradation products (including the maximum and the rest of the impurities). Therefore, the percentage of total impurity may be larger than that of the maximum impurity, unless there is only one degradation product found.

According to the pharmaceutical industry standard, the product is generally monitored under an accelerated condition at 40° C. and about 75% RH for three months, which is believed to represent about two years of product shelf life at room temperature. In the present invention, a more stressful condition, 60° C. and 75% RH for one week, was used as the accelerated condition to monitor the stability of pharmaceutical composition comprising bupropion hydrochloride and a stabilizer.

The stability of the formulations was tested by storage for one week at 60° C. and about 75% RH in 20 gram desiccant plastic bottles. It was found that formulations containing the stabilizers of the present invention retain at least 85% potency of the bupropion hydrochloride after the storage period. The precision for this potency measurement is 0.56% based on an assay determination of twelve tablets by a validated analytical method. Moreover, the maximum impurities in the formulation were less than about 0.1 and not more than about 0.5%. Further, the total impurities in the formulation were less than about 0.2% and not more than about 1% after storage. Stability of formulations was also tested after storage at 40° C. and 75% RH for four and twelve weeks.

Suitable stabilizers of the present invention include salts of organic bases such as creatinine hydrochloride, preferably having an aqueous pH of from about 2.70 to 3.10 at a concentration of about 10% w/w, thiamine hydrochloride, preferably having an aqueous pH of from about 2.95 to 3.05, at a concentration of about 20% w/w, pyridoxine hydrochloride, preferably having an aqueous pH of from about 2.70 to 2.72, at a concentration of about 20% w/w, and a salt of an inorganic acid such as potassium phosphate monobasic, preferably having an aqueous pH of from about 4.20 to 4.30 at a concentration of about 10% w/w. The aqueous pH of the stabilizers of this invention are determined by standard methods known in the art. See, for example, U.S. Pharmacopoeia Jan. 1, 2000, <791>, pps. 1977–1978. Other appropriate stabilizers may be chosen based on the stabilizer's ability to provide an acidic environment in the dosage form.

The suitable salts of organic bases that can stabilize bupropion hydrochloride in solid dosage include, but are not limited to, creatine hydrochloride, pyridoxine hydrochloride, and thiamine hydrochloride. The suitable salts of inorganic acids include, but are not limited to, potassium phosphate monobasic. It should be understood that combinations of stabilizers may be used that meet the aforementioned pH criteria.

Pharmaceutical compositions of the present invention may optionally include any conventional ingredients for improving the physical properties, visual appearance or odor of the pharmaceutical. Examples include, but are not limited to, lubricants such as talc or magnesium stearate; binders such as starch, hydroxypropyl cellulose, hydroxypropyl methyl cellulose, or polyvinylpyrrolidone; diluents such as microcrystalline cellulose or lactose; disintegrants such as sodium starch glycolate, crospovidone or croscarmellose sodium; glidants such as silicon dioxide; and colorants. Solid dosage forms may optionally be film coated.

The pharmaceutical composition prepared in accordance with the invention, preferably, is one wherein the weight of bupropion hydrochloride in the tablet, capsule, or caplet is Y where Y=25 mg to 500 mg and the amount of inactive ingredients is greater than about 180 to 190% of Y.

The total amount of inactive ingredient in the formulation, including the amount of stabilizer, is preferably about 186% of the amount of the bupropion hydrochloride in the composition, that is, the ratio of total inactive ingredients to bupropion hydrochloride in the formulation is about 1.86. The amount of stabilizer found in the inventive composition is preferably 28% to about 57% of the amount of bupropion hydrochloride in the formulation. The suitable amount of stabilizer is based on the stabilizer's ability to provide an acidic environment in the dosage form and can be determined by one of ordinary skill in the art.

Pharmaceutical compositions of the present invention may generally contain 25 mg to 500 mg of bupropion hydrochloride. Preferred compositions of the invention may contain 50 mg, 75 mg, 100 mg or 150 mg of active ingredient, and may be in the form of tablets, caplets or capsules. Immediate, modified, or extended release profiles, or combinations thereof, are also encompassed by the present invention.

Pharmaceutical compositions of the present invention may be prepared by making a dilute solution of organic base or inorganic acid, and adding the dilute organic base or inorganic acid solution to a dry blend of bupropion hydrochloride and other active ingredients. The mixture is granulated, dried and milled. Solid dosage formulations are prepared such as by compressing the milled granulation to form tablets or caplets. Alternatively, capsules may be prepared by placing the milled granulation in, for example, a two-part hard gelatin capsule.

More preferably, the pharmaceutical compositions in the present invention may be prepared by dry blending all the inactive ingredients and stabilizers with bupropion hydrochloride. Solid dosage form may then be prepared by compressing the powder into tablets.

EXAMPLES

The following examples are illustrative, but not limiting, of the present invention:

Example 1

Formulation and Stability of Bupropion Hydrochloride Sustained-Release Tablets Comprising Creatine Hydrochloride Formulation was calculated for a batch size of 0.25 kg, which yields approximately 581 tablets. The amount of each ingredient included in the formulation is shown in Table 1. All ingredients, except magnesium stearate, were passed through a size-reducing mill, a Comil® conical screen mill (Quadro Engineering Inc., Waterloo, Canada), equipped with a 0.09 inch opening stainless steel screen. The screened powder mix was then passed through a particle size separator equipped with a 1.3 mm opening stainless steel screen. The milled material was then charged into a slant-cone blender, and blended for twenty (20) minutes. Magnesium stearate was then screened through a No. 30 mesh USP standard sieve and added into the blend. The powder mix was then blended for another four (4) minutes, and compressed into tablets by a MANESTY® rotary betapress (BWI Manesty, Cheshire, UK), at a tablet weight of about 430 mg±3%. All tablets were packaged in plastic bottles with desiccants, and the bottles were heat sealed, then placed under the stress condition. Creatinine hydrochloride, a salt of an organic base, was included as a stabilizer.

Table 1 outlines the quantity of each constituent in a bupropion hydrochloride formulation which comprises 10% of creatinine hydrochloride.

TABLE 1

Formulation with 10% Creatinine Hydrochloride per Tablet

| Ingredient | Weight per tablet, mg |
|---|---|
| Bupropion hydrochloride | 150 |
| Microcrystalline cellulose, NF | 196.15 |
| Hydroxypropyl cellulose, NF | 34.40 |
| Creatinine hydrochloride, USP | 43 |
| Colloidal silicon dioxide, NF | 2.15 |
| Magnesium stearate, NF | 4.30 |
| TOTAL | 430.0 |

Formulations were prepared and stressed as described, and the stability of the bupropion hydrochloride was determined by HPLC measurement of impurities.

TABLE 2

Stability with 10% Creatinine Hydrochloride per Tablet

| | Percentage of maximum degradation product | Percentage of total degradation product | Potency, % |
|---|---|---|---|
| t = 0 | 0.00 | 0.00 | 95.15 |
| t = 1 wk 60° C./75% RH | 0.30 | 0.50 | 92.85 |
| t = 4 wks 40° C./75% RH | 0.076 | 0.076 | NA |
| t = 12 wks 40° C./75% RH | 0.112 | 0.112 | 99.70 |

These data indicate that about 90% of the original potency of bupropion hydrochloride was retained after 1 week at 60° C. and 75% RH in compositions containing 10% creatinine hydrochloride, and that nearly 100% of the original potency of bupropion hydrochloride was retained after 12 weeks at 40° C. and 75% RH in compositions containing 10% creatinine hydrochloride.

Therefore, these data show that creatinine hydrochloride is a suitable stabilizer for retaining potency of bupropion hydrochloride.

Example 2

Formulation and Stability of Bupropion Hydrochloride Sustained-Release Tablets Comprising Pyridoxine Hydrochloride Tablets were manufactured according to the procedure outlined in Example 1. Pyridoxine hydrochloride, a salt of an organic base, was included as a stabilizer.

Table 3 outlines the quantity of each constituent in a bupropion hydrochloride formulation which comprises 20% pyridoxine hydrochloride.

TABLE 3

Formulation with 20% Pyridoxine Hydrochloride per Tablet

| Ingredient | Weight per tablet, mg |
|---|---|
| Bupropion hydrochloride | 150 |
| Microcrystalline cellulose, NF | 153.15 |
| Hydroxypropyl cellulose, NF | 34.40 |

TABLE 3-continued

Formulation with 20% Pyridoxine Hydrochloride per Tablet

| Ingredient | Weight per tablet, mg |
|---|---|
| Pyridoxine hydrochloride, USP | 86 |
| Colloidal silicon dioxide, NF | 2.15 |
| Magnesium stearate, NF | 4.30 |
| TOTAL | 430.0 |

Two formulations comprising the stabilizer pyridoxine hydrochloride were tested. One, shown in Table 3, included 20% pyridoxine hydrochloride in each tablet. The stability of this formulation is illustrated in Table 4. Table 5 presents the stability of bupropion hydrochloride in a formulation in which pyridoxine hydrochloride made up 10% of each tablet.

TABLE 4

Stability with 20% pyridoxine Hydrochloride per Tablet

| | Percentage of maximum degradation product | Percentage of total degradation product | Potency, % |
|---|---|---|---|
| t = 0 | 0.00 | 0.00 | 100.03 |
| t = 1 wk 60° C./75% RH | 0.07 | 0.12 | 98.02 |
| t = 4 wks 40° C./75% RH | 0.026 | 0.026 | 106.6 |
| t = 12 wks 40° C./75% RH | NA | NA | NA |

TABLE 5

Stability with 10% Pyridoxine Hydrochloride per Tablet

| | Percentage of maximum degradation product | Percentage of total degradation product | Potency, % |
|---|---|---|---|
| t = 0 | 0.00 | 0.00 | 103.57 |
| t = 1 wk 60° C./75% RH | 0.08 | 0.11 | 99.70 |
| t = 4 wks 40° C./75% RH | 0.036 | 0.036 | NA |
| t = 12 wks 40° C./75% RH | 0.073 | 0.073 | 103.3 |

These data indicate that at least about 90% of the original potency of bupropion hydrochloride was retained after 1 week at 60° C. and 75% RH with either a 10% or 20% pyridoxine hydrochloride concentration; that about 100% of the original potency of bupropion hydrochloride was retained after 4 weeks at 40° C. and 75% RH with 20% pyridoxine hydrochloride concentration; and, that about 100% of the original potency was retained after 12 weeks at 40° C. and 75% RH with 10% pyridoxine hydrochloride.

These data thus show that pyridoxine hydrochloride is a suitable stabilizer for retaining potency of bupropion hydrochloride.

Example 3

Formulation and Stability of Bupropion Hydrochloride Sustained-Release Tablets Comprising Thiamine Hydrochloride Tablets were manufactured according to the process outlined in Example 1. Thiamine hydrochloride, a salt of an organic base, was included as a stabilizer.

Table 6 outlines the quantity of each constituent in a bupropion hydrochloride formulation which comprises 20% of thiamine hydrochloride.

TABLE 6

Formulation with 20% Thiamine Hydrochloride per Tablet

| Ingredient | Weight per tablet, mg |
| --- | --- |
| Bupropion hydrochloride | 150 |
| Microcrystalline cellulose, NF | 153.15 |
| Hydroxypropyl cellulose, NF | 34.40 |
| Thiamine hydrochloride, USP | 86 |
| Colloidal silicon dioxide, NF | 2.15 |
| Magnesium stearate, NF | 4.30 |
| TOTAL | 430.0 |

Two formulations were tested for stability. One, shown in Table 7, shows stability data for a formulation which contained 20% thiamine hydrochloride. The other, shown in Table 8, shows stability data for a formulation which contained 10% thiamine hydrochloride in each tablet.

TABLE 7

Stability with 20% Thiamine Hydrochloride per Tablet

| | Percentage of maximum degradation product | Percentage of total degradation product | Potency, % |
| --- | --- | --- | --- |
| t = 0 | 0.00 | 0.00 | 96.20 |
| t = 1 wk 60° C./75% RH | 0.09 | 0.12 | 96.14 |
| t = 4 wks 40° C./75% RH | 0.045 | 0.045 | 102.0 |
| t = 12 wks 40° C./75% RH | NA | NA | NA |

TABLE 8

Stability with 10% Thiamine Hydrochloride per Tablet

| | Percentage of maximum degradation product | Percentage of total degradation product | Potency, % |
| --- | --- | --- | --- |
| t = 0 | 0.00 | 0.00 | 98.49 |
| t = 1 wk 60° C./75% RH | 0.11 | 0.13 | 96.59 |
| t = 4 wks 40° C./75% RH | 0.070 | 0.070 | NA |
| t = 12 wks 40° C./75% RH | 0.065 | 0.065 | 101.5 |

These data indicate that at least about 90% of the original potency of bupropion hydrochloride was retained after 1 week at 60° C. and 75% RH using 20% and 10% thiamine hydrochloride, respectively; that about 100% of the original potency of bupropion hydrochloride was retained after 4 weeks at 40° C. and 75% RH with 20% thiamine hydrochloride; and that about 100% of the potency of bupropion hydrochloride was retained after 12 weeks at 40° C. and 75% RH with 10% thiamine hydrochloride.

Therefore, these data show that thiamine hydrochloride is a suitable stabilizer for retaining potency of bupropion hydrochloride.

Example 4

Formulation and Stability of Bupropion Hydrochloride Sustained-Release Tablets Comprising Potassium Phosphate Monobasic The formulation was manufactured according to the process outlined in Example 1. Potassium phosphate monobasic, a salt of an inorganic acid, was included as a stabilizer.

Table 9 outlines the quantity of each constituent in a bupropion hydrochloride formulation which comprises 10% Potassium Phosphate Monobasic.

TABLE 9

Formulation with 10% Potassium Phosphate Monobasic per Tablet

| Ingredient | Weight per tablet, mg |
| --- | --- |
| Bupropion hydrochloride | 150 |
| Microcrystalline cellulose, NF | 196.15 |
| Hydroxypropyl cellulose, NF | 34.40 |
| Potassium phosphate monobasic, NF | 43 |
| Colloidal silicon dioxide, NF | 2.15 |
| Magnesium stearate, NF | 4.30 |
| TOTAL | 430.0 |

TABLE 10

Stability with 10% Potassium Phosphate Monobasic per Tablet

| | Percentage of maximum degradation product | Percentage of total degradation product | Potency, % |
| --- | --- | --- | --- |
| t = 0 | 0.00 | 0.00 | 96.20 |
| t = 1 wk 60° C./75% RH | 0.14 | 0.19 | 97.48 |
| t = 4 wks 40° C./75% RH | 0.084 | 0.084 | 100 |
| t = 12 wks 40° C./75% RH | NA | NA | NA |

These data indicate that at least about 90% of the original potency of bupropion hydrochloride was retained after 1 week at 60° C. and 75% RH using potassium phosphate monobasic as a stabilizer, and that about 100% of the original potency of bupropion hydrochloride was retained after 4 weeks at 40° C. and 75% RH using potassium phosphate monobasic as a stabilizer.

These data indicate that potassium phosphate monobasic is a suitable stabilizer for retaining potency of bupropion hydrochloride.

Example 5

Formulation and Stability of Bupropion Hydrochloride Sustained-Release Tablets

Table 11 outlines the quantity of each constituent in a bupropion hydrochloride formulation which comprises no stabilizing agents.

TABLE 11

Formulation with No Stabilizer per Tablet

| Ingredient | Weight per tablet, mg |
|---|---|
| Bupropion hydrochloride | 150 |
| Microcrystalline cellulose, NF | 239.15 |
| Hydroxypropyl cellulose, NF | 34.40 |
| Colloidal silicon dioxide, NF | 2.15 |
| Magnesium stearate, NF | 4.30 |
| TOTAL | 430.0 |

Table 12 shows stability data for a formulation which contained no stabilizer.

TABLE 12

Stability with No Stabilizer per Tablet

| | Percentage of maximum degradation product | Percentage of total degradation product | Potency, % |
|---|---|---|---|
| t = 0 | 0.00 | 0.00 | 92.19 |
| t = 1 wk 60° C./75% RH | 0.31 | 0.31 | 88.05 |
| t = 4 wks 40° C./75% RH | 0.115 | 0.115 | 98.8 |
| t = 12 wks 40° C./75% RH | 0.146 | 0.146 | 96.4 |

These data indicate that about 80% of the original potency of bupropion hydrochloride was retained after 1 week at 60° C. and 75% RH using no stabilizer in the composition, and about 80% of the original potency of bupropion hydrochloride was retained after 4 and 12 weeks at 40° C. and 75% RH.

Therefore, under the stability test, the potency of bupropion hydrochloride is not as well retained when compared with the stability of the formulations of the present invention.

Example 6

Comparison of Various Stabilizers by Potency

Sustained release tablets comprising bupropion hydrochloride and several types of stabilizers were manufactured according to the process outlined in Example 1, and stressed for one week at 60° C. and 75% RH. Table 13 illustrates the level of maximum and total impurities of each formulation, with the amount of stabilizer indicated as the percentage of tablet weight. Formulations were prepared and stressed as described, and the stability of the bupropion hydrochloride was determined by HPLC measurement of impurities.

TABLE 13

Maximum and Total Impurities of Bupropion Hydrochloride Formulations

| Stabilizer | % by weight | Maximum impurity, % | Total Impurity, % |
|---|---|---|---|
| Creatinine hydrochloride | 10 | NA | 0.50 |
| Pyridoxine hydrochloride | 20 | 0.07 | 0.12 |
| Thiamine hydrochloride | 20 | 0.09 | 0.12 |
| Potassium phosphate monobasic | 10 | 0.14 | 0.19 |
| None | — | 0.31 | 0.31 |

Table 14 illustrates the remaining potency of bupropion hydrochloride of formulations stressed as described for Table 13.

TABLE 14

Potency of Bupropion Hydrochloride Formulations

| Stabilizer | % by Weight | Potency, % |
|---|---|---|
| Creatine hydrochloride | 10 | 92.85 |
| Pyridoxine hydrochloride | 10 | 99.70 |
| Pyridoxine hydrochloride | 20 | 98.02 |
| Thiamine hydrochloride | 10 | 96.59 |
| Thiamine hydrochloride | 20 | 96.14 |
| Potassium phosphate monobasic | 10 | 97.48 |
| None | — | 88.05 |

The data of Table 13 indicate that compositions containing either 20% of pyridoxine hydrochloride or 20% thiamine hydrochloride resulted in the lowest amounts of total impurities after one week at 60° C. and 75% RH. Table 14 shows that compositions containing either 10% or 20% of pyridoxine hydrochloride exhibited the highest level of potency of bupropion hydrochloride after one week at 60° C. and 75% RH. Thus, these data verify a distinct improvement over other known approaches, which provide a bupropion hydrochloride composition where only 80% of potency of bupropion hydrochloride is retained after storage at 40° C. and 75% RH.

While there has been described what is presently believed to be the preferred embodiments of the present invention, other and further modifications and changes may be made without departing from the spirit of the invention. We intend to include all further and other modifications and changes which come within the scope of the invention as set forth in the claims. The disclosure of all publications cited above are expressly incorporated by reference in their entireties to the same extent as if each were incorporated by reference individually.

We claim:

1. A pharmaceutical composition comprising bupropion hydrochloride and a pharmaceutically acceptable stabilizer in an effective stabilizing amount, in which at least about 80% of an initial potency of said bupropion hydrochloride in the composition is maintained after storage for one week at 60° C. and 75% relative humidity.

2. A pharmaceutical composition comprising bupropion hydrochloride and a pharmaceutically acceptable stabilizer in an effective stabilizing amount, in which at least about 80% of an initial potency of said bupropion hydrochloride in the composition is maintained after storage for one week at 60° C. and 75% relative humidity, and, wherein said stabilizer is selected from the group consisting of a salt of an organic base and a salt of an inorganic acid.

3. The pharmaceutical composition of claim 2, wherein said salt of an organic base is selected from the group consisting of creatinine hydrochloride, pyridoxine hydrochloride and thiamine hydrochloride.

4. The pharmaceutical composition of claim 2, wherein said salt of an inorganic acid is potassium phosphate monobasic.

5. The composition of claim 1, in which at least about 85% of an initial potency of said bupropion hydrochloride in the composition is maintained after storage for one week at 60° C. and 75% relative humidity.

6. The composition of claim 5, in which at least about 90% of an initial potency of said bupropion hydrochloride in the composition is maintained after storage for one week at 60° C. and 75% relative humidity.

7. The composition of claim 6 in which at least about 95% of an initial potency of said bupropion hydrochloride in the composition is maintained after storage for one week at 60° C. and 75% relative humidity.

8. The composition of claim 7, in which at least about 98% of an initial potency of said bupropion hydrochloride in the composition is maintained after storage for one week at 60° C. and 75% relative humidity.

9. A method of stabilizing bupropion hydrochloride in a pharmaceutical composition so that at least about 80% of the potency of bupropion hydrochloride is maintained after storage for one week at 60° C. and 75% relative humidity, wherein said method comprises the step of mixing bupropion hydrochloride with a pharmaceutically acceptable stabilizer in an effective stabilizing amount.

10. The method of claim 9 where the step of mixing utilizes a dry blend of said bupropion hydrochloride, said pharmaceutically acceptable stabilizer, and other pharmaceutically acceptable excipients.

11. A method of stabilizing bupropion hydrochloride in a pharmaceutical composition so that at least about 80% of the potency of the bupropion hydrochloride is maintained after storage for one week at 60° C. and 75% relative humidity, wherein said method comprises the step of mixing bupropion hydrochloride with a pharmaceutically acceptable stabilizer in an effective stabilizing amount and, where the step of mixing utilizes a dry blend of said bupropion hydrochloride, said pharmaceutically acceptable stabilizer, and other pharmaceutically acceptable excipients.

12. The method of claim 11, wherein said salt of an organic base is selected from the group consisting of creatinine hydrochloride, pyridoxine hydrochloride and thiamine hydrochloride.

13. The method of claim 11, wherein said salt of an inorganic acid is potassium phosphate monobasic.

14. The method of claim 9, in which at least about 85% of an initial potency of said bupropion hydrochloride in the composition is maintained after storage for one week at 60° C. and 75% relative humidity.

15. The method of claim 9, in which at least about 90% of an initial potency of said bupropion hydrochloride in the composition is maintained after storage for one week at 60° C. and 75% relative humidity.

16. The method of claim 15, in which at least about 95% of an initial potency of said bupropion hydrochloride in the composition is maintained after storage for one week at 60° C. and 75% relative humidity.

17. The method of claim 16, in which at least about 98% of an initial potency of said bupropion hydrochloride in the composition is maintained after storage for one week at 60° C. and 75% relative humidity.

18. A pharmaceutical composition comprising bupropion hydrochloride and a pharmaceutically acceptable stabilizer in an effective stabilizing amount, in which at least 80% of an initial potency of said bupropion hydrochloride in the composition is maintained after storage for 4 or 12 weeks at 60° C. and 75% relative humidity.

19. A pharmaceutical composition comprising bupropion hydrochloride and a pharmaceutically acceptable stabilizer in an effective stabiling amount, in which at least about 80% of an initial potency of said bupropion hydrochloride in the composition is maintained after storage for 4 or 12 weeks at 40° C. and 75% relative humidity, and, wherein said stabilizer is a salt of an organic base or a salt of an inorganic acid.

20. The pharmaceutical composition of claim 19, wherein said salt of an organic base is selected from the group consisting of creatinine hydrochloride, pyridoxine hydrochloride and thiamine hydrochloride.

21. The pharmaceutical composition of claim 19, wherein said salt of an inorganic acid is potassium phosphate monobasic.

22. The pharmaceutical composition of claim 18, in which at least about 85% of an initial potency of said bupropion hydrochloride in the composition is maintained after storage for 4 weeks at 60° C. and 75% relative humidity.

23. The composition of claim 18, in which at least about 85% of an initial potency of said bupropion hydrochloride in the composition is maintained after storage for 12 weeks at 60° C. and 75% relative humidity.

24. The composition of claim 18, in which at least about 90% of an initial potency of said bupropion hydrochloride in the composition is maintained after storage for 4 weeks at 60° C. and 75% relative humidity.

25. The composition of claim 18, in which at least about 90% of an initial potency of said bupropion hydrochloride in the composition is maintained after storage for 12 weeks at 60° C. and 75% relative humidity.

26. The composition of claim 24, in which at least about 95% of an initial potency of said bupropion hydrochloride in the composition is maintained after storage for 4 weeks at 60° C. and 75% relative humidity.

27. The composition of claim 25, in which at least about 95% of an initial potency of said bupropion hydrochloride in the composition is maintained after storage for 12 weeks at 60° C. and 75% relative humidity.

28. The composition of claim 26, in which at least about 98% of an initial potency of said bupropion hydrochloride in the composition is maintained after storage for 4 weeks at 60° C. and 75% relative humidity.

29. The composition of claim 27, in which at least about 98% of an initial potency of said bupropion hydrochloride in the composition is maintained after storage for 12 weeks at 60° C. and 75% relative humidity.

30. A method of stabilizing bupropion hydrochloride in a pharmaceutical composition so that at least 80% of the potency of bupropion hydrochloride is maintained after storage for 4 or 12 weeks at 60° C. and 75% relative humidity, wherein said method comprises the step of mixing a dry blend of bupropion hydrochloride with a pharmaceutically acceptable stabilizer in an effective stabilizing amount.

31. A method of stabilizing bupropion hydrochloride in a pharmaceutical composition so that at least 80% of the potency of the bupropion hydrochloride is maintained after storage for 4 or 12 weeks at 40° C. and 75% relative humidity, wherein said method comprises the step of mixing a dry blend of bupropion hydrochloride with a pharmaceutically acceptable stabilizer in an effective stabilizing amount, and, wherein said stabilizer is a salt of an organic base or a salt of an inorganic acid.

32. The method of claim 31, wherein said salt of an organic base is selected from the group consisting of creatinine hydrochloride, pyridoxine hydrochloride and thiamine hydrochloride.

33. The method of claim 32, wherein said salt of an inorganic acid is potassium phosphate monobasic.

34. The method of claim 30, wherein at least about 85% of an initial potency of said bupropion hydrochloride in the composition is maintained after storage for 4 weeks at 60° C. and 75% relative humidity.

35. The method of claim 30, wherein at least about 85% of an initial potency of said bupropion hydrochloride in the composition is maintained after storage for 12 weeks at 60° C. and 75% relative humidity.

36. The method of claim 30, wherein at least about 90% of an initial potency of said bupropion hydrochloride in the composition is maintained after storage for 4 weeks at 60° C. and 75% relative humidity.

37. The method of claim 30, wherein at least about 90% of an initial potency of said bupropion hydrochloride in the composition is maintained after storage for 12 weeks at 60° C. and 75% relative humidity.

38. The method of claim 36, wherein at least about 95% of an initial potency of said bupropion hydrochloride in the composition is maintained after storage for 4 weeks at 60° C. and 75% relative humidity.

39. The method of claim 37, wherein at least about 95% of an initial potency of said bupropion hydrochloride in the composition is maintained after storage for 12 weeks at 60° C. and 75% relative humidity.

40. The method of claim 38, wherein at least about 98% of an initial potency of said bupropion hydrochloride in the composition is maintained after storage for 4 weeks at 60° C. and 75% relative humidity.

41. The method of claim 39, wherein at least about 98% of an initial potency of said bupropion hydrochloride in the composition is maintained after storage for 12 weeks at 60° C. and 75% relative humidity.

42. A pharmaceutical composition comprising bupropion hydrochloride and a pharmaceutically acceptable stabilizer in an effective stabilizing amount, in which the stabilizer is selected from the group consisting of an organic base and a salt of an inorganic acid.

43. The composition of claim 42, wherein said salt of an organic base is selected from the group consisting of creatinine hydrochloride, pyridoxine hydrochloride and thiamine hydrochloride.

44. The composition of claim 42, wherein said salt of an inorganic acid is potassium phosphate monobasic.

45. The composition of claim 42, in which at least about 85% of an initial potency of said bupropion hydrochloride in the composition is maintained after storage for one week at 60° C. and 75% relative humidity.

46. The composition of claim 42, in which at least about 90% of an initial potency of said bupropion hydrochloride in the composition is maintained after storage for one week at 60° C. and 75% relative humidity.

47. The composition of claim 46, in which at least about 95% of an initial potency of said bupropion hydrochloride in the composition is maintained after storage for one week at 60° C. and 75% relative humidity.

48. The composition of claim 47, in which at least about 98% of an initial potency of said bupropion hydrochloride in the composition is maintained after storage for one week at 60° C. and 75% relative humidity.

49. A pharmaceutical composition comprising bupropion hydrochloride and a pharmaceutically acceptable stabilizer in an effective stabilizing amount, in which the stabilizer is selected from the group consisting of an organic base and a salt of an inorganic acid, and in which at least about 80% of an initial potency of said bupropion hydrochloride in the composition is maintained after storage for one week at 60° C. and 75% relative humidity.

50. The pharmaceutical composition of claim 49, wherein said salt of an organic base is selected from the group consisting of creatinine hydrochloride, pyridoxine hydrochloride and thiamine hydrochloride.

51. The pharmaceutical composition of claim 49, wherein said salt of an inorganic acid is potassium phosphate monobasic.

52. The composition of claim 49, in which at least about 85% of an initial potency of said bupropion hydrochloride in the composition is maintained after storage for one week at 60° C. and 75% relative humidity.

53. The composition of claim 49, in which at least about 90% of an initial potency of said bupropion hydrochloride in the composition is maintained after storage for one week at 60° C. and 75% relative humidity.

54. The composition of claim 53, in which at least about 95% of an initial potency of said bupropion hydrochloride in the composition is maintained after storage for one week at 60° C. and 75% relative humidity.

55. The composition of claim 54, in which at least about 98% of an initial potency of said bupropion hydrochloride in the composition is maintained after storage for one week at 60° C. and 75% relative humidity.

\* \* \* \* \*